US009661844B2

(12) United States Patent
Aulisa et al.

(10) Patent No.: US 9,661,844 B2
(45) Date of Patent: May 30, 2017

(54) PESTICIDE COMPOSITION DELIVERY VEHICLES

(71) Applicant: Dow AgroSciences LLC, Indianapolis, IN (US)

(72) Inventors: Lorenzo Aulisa, Carmel, IN (US); John D. Busacca, Noblesville, IN (US); Donald E. Williams, III, Greenfield, IN (US); Phillip J. Howard, Zionsville, IN (US); Ashish Batra, Indianapolis, IN (US); Sara J. Linder, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 13/870,023

(22) Filed: Apr. 25, 2013

(65) Prior Publication Data

US 2013/0287830 A1   Oct. 31, 2013

Related U.S. Application Data

(60) Provisional application No. 61/640,392, filed on Apr. 30, 2012.

(51) Int. Cl.

| | | |
|---|---|---|
| *A01N 25/02* | (2006.01) | |
| *A01N 25/04* | (2006.01) | |
| *A01N 25/34* | (2006.01) | |
| *A01N 29/02* | (2006.01) | |

(52) U.S. Cl.
CPC ............. *A01N 25/02* (2013.01); *A01N 25/04* (2013.01); *A01N 25/34* (2013.01)

(58) Field of Classification Search
CPC ........ A01N 29/02; A01N 25/34; A01N 25/28; A01N 25/02; Y10S 514/963
See application file for complete search history.

(56) References Cited

U.S. PATENT DOCUMENTS

| | | | | |
|---|---|---|---|---|
| 2,543,580 | A | | 2/1951 | Kay et al. |
| 2,870,062 | A | * | 1/1959 | Stanley et al. ................ 424/456 |
| 3,159,536 | A | * | 12/1964 | Marotta ................. A01N 55/00 424/406 |
| 3,639,259 | A | | 2/1972 | Scarpelli |
| 3,640,234 | A | | 2/1972 | Carroll et al. |
| 4,078,089 | A | * | 3/1978 | Levek .................... A01N 29/02 424/125 |
| 4,780,316 | A | * | 10/1988 | Brox ............................. 424/456 |
| 4,808,206 | A | | 2/1989 | Smith |
| 4,971,796 | A | * | 11/1990 | Sjogren ......................... 424/417 |
| 5,190,764 | A | * | 3/1993 | Chiba et al. .................. 424/408 |
| 5,292,533 | A | | 3/1994 | McHahon et al. |
| 5,466,460 | A | | 11/1995 | McMahon et al. |
| 6,045,835 | A | | 4/2000 | Soper et al. |
| 6,224,905 | B1 | * | 5/2001 | Lawrence et al. ............ 424/464 |
| 2001/0036472 | A1 | * | 11/2001 | Wong et al. .................. 424/456 |
| 2002/0061325 | A1 | * | 5/2002 | Ingram et al. ................ 424/408 |
| 2004/0224020 | A1 | | 11/2004 | Schoenhard |
| 2005/0058703 | A1 | | 3/2005 | Chang et al. |
| 2005/0079215 | A1 | | 4/2005 | Schleifenbaum et al. |
| 2005/0214337 | A1 | | 9/2005 | McGee et al. |
| 2006/0110442 | A1 | | 5/2006 | Wonschik et al. |
| 2007/0172523 | A1 | | 7/2007 | Hashitera et al. |
| 2009/0029863 | A1 | | 1/2009 | Nugent et al. |
| 2010/0266685 | A1 | | 10/2010 | Machinek et al. |
| 2010/0266686 | A1 | | 10/2010 | Horn et al. |
| 2011/0005914 | A1 | | 1/2011 | Trippeer et al. |
| 2011/0059165 | A1 | | 3/2011 | Gaserod et al. |
| 2012/0021032 | A1 | | 1/2012 | Aubert et al. |
| 2012/0049410 | A1 | | 3/2012 | Altamar et al. |

FOREIGN PATENT DOCUMENTS

| | | |
|---|---|---|
| CA | 476979D | 9/1951 |
| CN | 1141147 | 1/1997 |
| CN | 1507321 | 6/2004 |
| CN | 101480178 | 7/2009 |
| CN | 101480179 | 7/2009 |
| CN | 101480180 | 7/2009 |
| CN | 101480181 | 7/2009 |
| CN | 101491242 | 7/2009 |
| CN | 101491244 | 7/2009 |

(Continued)

OTHER PUBLICATIONS

Wang (Journal of Agricultural and Food Chemistry, 2010, vol. 58, pp. 361-365).*
Singh et al (Pharmaceutical Technology, Apr. 2002, pp. 36-58).*
International Search Report dated Apr. 25, 2013 from application No. PCT/US2013/65789.
Patent Cooperation Treaty International Search Report and Written Opinion of the International Searching Authority. PCT Patent Application No. PCT/US2013/038103, Apr. 25, 2013.
Meyer, M. C. et al. (2008). The Effect of Gelatin Cross-Linking on the Bioequivalence of Hard and Soft Gelatin Acetaminophen Capsules. Pharmaceutical Research, 17(8), 962-966. (5 pages).
Ofner, C. M., et al. (2001). Crosslinking studies in gelatin capsules treated with formaldehyde and in capsules exposed to elevated temperature and humidity. Journal of Pharmaceutical Sciences J. Pharm. Sci., 90(1), 79-88. (10 pages).

*Primary Examiner* — Mark V Stevens
(74) *Attorney, Agent, or Firm* — Carl D. Corvin; Maschoff Brennan (57) ABSTRACT

Vehicles for delivery and release of pesticide compositions are provided. In one aspect, the delivery vehicle is a capsule configured to resist release of a pesticide composition before application of the capsule at a locus where pest control is desired. The capsule is further configured to degrade following application at the locus where pest control is desired to facilitate release of the pesticide composition. In one particular but non-limiting form, the capsule includes a shell wall including a relatively high Bloom strength gelatin material and a plasticizer material, and the pesticide composition includes a fumigant such as 1,3-dichloropropene. Further embodiments, forms, objects, features, advantages, aspects, and benefits shall become apparent from the description and drawings.

17 Claims, 3 Drawing Sheets

(56) References Cited

FOREIGN PATENT DOCUMENTS

| | | |
|---|---|---|
| CN | 101584314 | 11/2009 |
| EP | 0515070 A1 | 11/1992 |
| EP | 0622069 A1 | 11/1994 |
| GB | 2265594 A * | 10/1993 |
| JP | 5645401 | 4/1981 |
| JP | 5626802 | 9/1981 |
| JP | 2002360665 | 12/2002 |
| JP | 2009280551 | 12/2009 |
| JP | 2010254620 | 11/2010 |
| JP | 2010531659 | 11/2010 |
| TW | I402034 | 7/2013 |
| WO | 95/22253 | 8/1995 |
| WO | 2006/053577 | 5/2006 |
| WO | 2006053577 A1 | 5/2006 |
| WO | 2007/056299 | 5/2007 |
| WO | 2007/081961 | 7/2007 |
| WO | 2008/134744 | 11/2008 |
| WO | 2008/142637 A1 | 11/2008 |

* cited by examiner

PESTICIDE COMPOSITION DELIVERY VEHICLES

CROSS-REFERENCE TO RELATED APPLICATIONS

The present application claims priority to U.S. Provisional Patent Application No. 61/640,392 filed Apr. 30, 2012, the content of which is incorporated herein by reference in its entirety.

BACKGROUND

The present application relates to vehicles configured to deliver and release pesticide compositions in a controlled manner, and more particularly but not exclusively, to degradable capsules formed of a gelatin material and encapsulating a pesticide composition.

Fields, groves, orchards and other plant growing environments can be infested with various pests, non-limiting examples of which include soil-borne plant pathogens and/or plant parasitic nematodes. When such infestations involve soil-borne plant pathogens and/or plant parasitic nematodes, soil fumigation is often the best or only economical method of reducing these pest populations sufficiently to produce high quality and high yielding plant crops, including for example fruits and vegetables. In one application technique, a fumigant in a liquid or vapor phase is injected into the soil through a delivery nozzle inserted into the soil to a desired depth. When injected in a liquid phase, the fumigant converts to a gas that spreads out in the soil surrounding the site of injection.

In most instances, the application of fumigants utilizing this technique yields acceptable control of targeted pests. However, it is not free from shortcomings and undesirable side effects. For example, one problem that arises in connection with the use of this technique is exposure of workers to noxious and dangerous fumes. Another problem with this technique is that a significant portion of the volatile substances in the fumigants commonly escape into the atmosphere. This is often due to the inability to precisely control the dosage and/or release of the fumigant. In turn, ground level ozone is generated from the reaction of the volatile fumigant with nitrogen oxides in the troposphere, and it can be harmful to respiratory systems of animals and damage sensitive plants. It is also believed that volatile substances used in certain fumigants may play a role in global ozone depletion in the Earth's upper atmosphere, which is known to be associated with a variety of negative consequences.

To reduce the loss of fumigants into the atmosphere, and the resulting loss of fumigant efficacy, a covering material such as a polyethylene sheet or tarp is sometimes utilized to cover the soil after application of the fumigant. The polyethylene tarp, although not impervious to gases, can reduce the dissipation rate of gases into the air, and thus prevent the depletion of the volatile fumigants by evaporation into the atmosphere. Nonetheless, covering the soil with these materials is labor-intensive, complicated and requires special application equipment, and workers are still exposed to noxious and dangerous fumes. In addition, the use of capsules which contain the fumigant and are applied via implantation into the soil has been advanced as an approach for overcoming the above identified shortcomings and undesirable side effects. However, even with these advances, controlling the release of fumigant from the capsule is problematic. For example, in many cases the fumigant is untimely released, in whole or in part, during shipping, storage or other handling of the capsules. This leads to decreased effectiveness of the implanted capsules and also exposes workers handling the capsules to the fumigant. In addition, control of the time and rate at which the fumigant is released following implantation of the capsule into the soil is still inadequate, and ground level ozone can still be present in some instances. Accordingly, there is a demand for further improvements in this area of technology.

SUMMARY

Vehicles for delivery and release of pesticide compositions are provided. In one aspect, the delivery vehicle is a capsule configured to resist release of a pesticide composition before application of the capsule at a locus where pest control is desired. The capsule is further configured to degrade following application at the locus where pest control is desired to facilitate release of the pesticide composition. In one particular but non-limiting form, the capsule includes a shell wall including a relatively high Bloom strength gelatin material and a plasticizer material, and the pesticide composition includes a fumigant such as 1,3-dichloropropene.

In one embodiment, a capsule includes a shell wall encapsulating a pesticide composition and including a gelatin material having a Bloom strength in the range of 250 to 300 grams. The shell wall also includes a plasticizer composition, and the gelatin material and the plasticizer composition are present at a ratio by weight between 2:1 and 4:1.

In another embodiment, a process includes positioning a capsule at a locus to control pests. The capsule includes a shell wall encapsulating a pesticide composition and including a gelatin material having a Bloom strength in the range of 250 to 300 grams. The shell wall also includes a plasticizer composition, and the gelatin material and the plasticizer composition are present at a ratio by weight between 2:1 and 4:1. In one form, the process also includes applying a protease enzyme dissolved in water to the capsule before it is positioned at the locus.

In yet another embodiment, a capsule includes a shell wall including a gelatin material and a plasticizer composition which includes a mixture of sorbitol and mannitol. The capsule also includes a pesticide composition encapsulated by the shell wall. The pesticide composition includes a fumigant and a fumed silica material.

In still another embodiment, a capsule includes a shell wall which is formed by a gelatin composition and encapsulates a pesticide composition. The pesticide composition includes a fumigant, a fumed silica material and a dialdehyde cross-linking agent.

In another embodiment, a process includes providing a first mixture including a fumed silica material and 1,3-dichloropropene; providing a second mixture including type-B gelatin and a plasticizer including a mixture of sorbitol, mannitol and sorbitol anhydrides; and encapsulating the first mixture in the second mixture using a rotary die apparatus.

Other aspects include unique methods, systems, devices, kits, assemblies, equipment, and/or apparatus related to delivery and release of pesticide compositions.

Further aspects, embodiments, forms, features, benefits, objects, and advantages shall become apparent from the detailed description and figures provided herewith.

DETAILED DESCRIPTION OF REPRESENTATIVE EMBODIMENTS

For purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Vehicles for delivery and release of pesticide compositions are provided. As used herein the term "pesticide" is intended to encompass herbicides, fungicides, insecticides and bactericides. Similarly, depending on the particular form of the pesticide composition, pests that can be targeted by the disclosed delivery vehicles include insects, plant pathogens, weeds, molluscs, nematodes, and microbes. It should be appreciated however that the foregoing are merely non-limiting examples.

In one aspect, the delivery vehicle is a capsule configured to resist release of a pesticide composition before application of the capsule at a locus where pest control is desired. The capsule is further configured to degrade following application at the locus where pest control is desired to facilitate release of the pesticide composition. In certain forms, the capsule is also configured to control various aspects of the release of the pesticide composition, including for example its time and rate of release. In one particular but non-limiting form, the capsule includes a shell wall including a relatively high Bloom strength gelatin material and a plasticizer material, and the pesticide composition includes a fumigant such as 1,3-dichloropropene.

Figure 1:
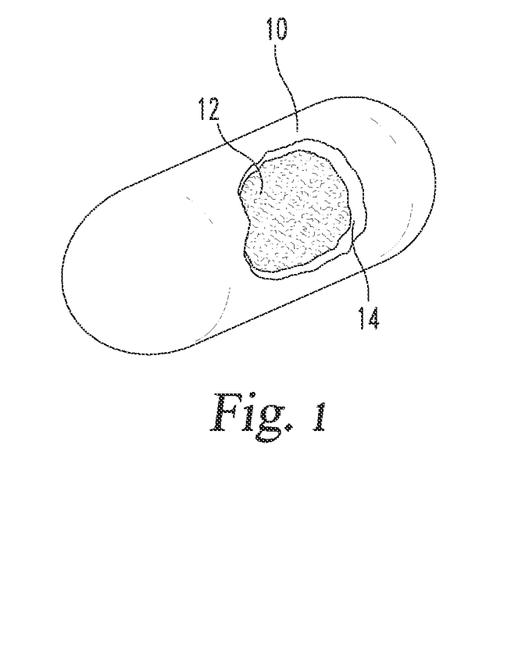
FIG. 1 is a perspective, partially exploded view of a capsule for delivery of a pesticide composition.

Turning now to FIG. 1, a partial cut away view of one non-limiting form of a capsule 10 including a pesticide composition 12 is illustrated. Capsule 10 includes an external shell wall 14 which surrounds and encapsulates pesticide composition 12. In the illustrated form, shell wall 14 provides capsule 10 with a tablet or pill shape such that it is generally cylindrically shaped with hemispherical ends. However, it should be understood that different forms and shapes for capsule 10 are envisioned. For example, capsule 10 may be circular, spherical, oval, oblong oval, square, rectangular, disc-shaped, football-shaped, puck-shaped, or rod-shaped, just to provide a few non-limiting possibilities.

Shell wall 14 includes a gelatin material which may be selected from any of a number suitable possibilities. More particularly, non-limiting gelatin materials which may be used for shell wall 14 include type-A gelatin which is derived from collagen by an acid pretreatment process and type-B gelatin which is derived from collagen by an alkaline pretreatment process. Exemplary collagen sources from which type-A gelatin and type-B gelatin can be obtained include fish, and bovine and porcine bones and hides. It is also contemplated that the gelatin material included in shell wall 14 could have side chains which have been modified through succination, carboxymethylation, carboxyethylation, methylation, hydroxyethylation, or acetylation, just to provide a few examples. In addition, it should be appreciated that shell wall 14 is not limited to the inclusion of a single type of gelatin material.

A variety of different gel strengths for the gelatin material included in shell wall 14 are possible. Gel strength may be measured using a Bloom Gelometer, and measured values of Bloom strength have units of grams and serve as relative indicators of the strength of a gel as a function of resistance of the gel to penetration by a probe. One test procedure for determining Bloom strength is disclosed in *Industrial and Engineering Chemistry, Analytical Edition*, Volume II, Page 348. In one form, the gelatin material of shell wall 14 has a Bloom strength that is greater than 200 grams. In another form, the gelatin material of shell wall 14 has a Bloom strength in the range of 220 to 300 grams. In another form, the gelatin material of shell wall 14 has a Bloom strength in the range of 250 to 300 grams. In still another form, the gelatin material of shell wall 14 has a Bloom strength in the range of 270 to 300 grams. However, it should be appreciated that alternative values for the Bloom strength of the gelatin material of shall wall 14 are possible and contemplated.

In one particular form, shell wall 14 may only include the gelatin material. However, in other forms shell wall 14 includes one or more materials in addition to the gelatin material. In these forms, the gelatin material may be present in the range of 40%-90% by weight based on the total weight of shell wall 14. In another form, the gelatin material is present in the range of 50%-80% by weight based on the total weight of shell wall 14. In yet another form, the gelatin material is present in the range of 60%-70% based on the total weight of shell wall 14. It should be understood however that other values for the amount of the gelatin material included in shell wall 14 are contemplated.

Materials in shell wall 14 in addition to the gelatin material may be present to provide desired capsule forming properties and/or to modify various properties of capsule 10. For example, the additional material(s) may alter capsule elasticity or degradation profiles of shell wall 14, or increase capsule stability by, for example, enhancing thermal stability, light stability, and corrosion resistance. It should be appreciated that the release profile of capsule 10 may be affected as a result of undertaking one or more of the above modifications to the properties of capsule 10. Similarly, it should be understood that one or more of these properties can be modified in order to provide capsule 10 with release characteristics tailored for particular applications.

Non-limiting examples of additional materials that can be included in shell wall 14 include additional polymer materials, ultraviolet absorbents, preservatives, a plasticizer, a disintegrant to promote degradation of capsule 10 and a cross-linking agent to stiffen the structure of shell wall 14. More particular examples of additional polymer materials that can be included in shell wall 14 include polyvinyl alcohol, polyethylene oxide, alginate, propylene and glycol alginate. Non-limiting examples of cross-linking agents that can be included in shell wall 14 are aldehydes such as glutaraldehyde, and starch and starch derivatives can be used as disintegrants. More particular examples of plasticizers that can be included in shell wall 14 include corn syrup solids, polyethylene glycol, ethylene glycol, sucrose, mannitol, glycerol, fructose, sorbitol, cellulose, cyclodextrins, maltodextrins, dioctyl-sodium sulfosuccinate, triethyl citrate, tributyl citrate, 1,2-propylenglycol, mono-, di- or tri-acetates of glycerol, natural gums or the like as well as mixtures of the foregoing.

In one particular but non-limiting form, shell wall 14 includes a plasticizer in addition to the gelatin material, and the plasticizer is a composition including a mixture of sorbitol, mannitol, and sorbitol anhydrides. One particular form of this type of plasticizer is available commercially from SPI Pharma (Wilmington, Del.) as Sorbitol Special™. When shell wall 14 includes the gelatin material and a plasticizer, they may be present relative to one another at a ratio by weight between 1:1 and 5:1. In another form, the gelatin material and the plasticizer are present at a ratio by weight between 2:1 and 4:1. In still another form, the gelatin material and the plasticizer are present at a ratio by weight between 3:1 and 3.5:1, although further variations in the ratio by weight between the gelatin material and the plasticizer are possible.

Pesticide composition 12 can be of any form suitable for release from capsule 10. In one particular but non-limiting form, pesticide composition 12 includes a fumigant. Fumigants are pesticides that have a relatively high vapor pressure and hence can exist as a gas in sufficient concentrations to kill pests in soil or enclosed spaces. The toxicity of the fumigant is proportional to its concentration and the exposure time. They are characterized by a good capacity for diffusion and act by penetrating the pest's respiratory system or being absorbed through the pest's cuticle. Exemplary fumigants that can be included in pesticide composition 12, either alone or in any suitable combination, include trichloronitromethane, 1,2-dichloropropane, 1,3-dichloropropene, ethylene dibromide, and methyl bromide. In one particular but non-limiting form, the fumigant includes 1,3-dichloropropene. One particular form of this type of fumigant is available commercially from Dow AgroSciences, LLC (Indianapolis, Ind.) as Telone®. In one form in which pesticide composition 12 includes a fumigant, the fumigant is present in the range of 50%-90% by weight based on the total weight of capsule 10. In another form, the fumigant is present in the range of 60%-80% by weight based on the total weight of capsule 10. In yet another form, the fumigant is present in the range of 65%-75% by weight based on the total weight of capsule 10, although other values for the weight percentage of the fumigant are contemplated.

Pesticide composition 12 may also include one or more materials or components in addition to the pesticide. These components include, but are not limited to, (this is a non-exhaustive and non-mutually exclusive list) spreaders, stickers, penetrants, buffers, sequestering agents, drift reduction agents, compatibility agents, anti-foam agents, preservation agents, cleaning agents, thickeners, cross-linking agents, and anti-foam agents. In one particular form, pesticide composition 12 includes a thickener in addition to the pesticide. Examples of these types of materials, include, but are limited to, a montmorillonite such as bentonite, silica materials, guar gum, locust bean gum, carrageenam, alginates, methyl cellulose, sodium carboxymethyl cellulose (SCMC), and hydroxyethyl cellulose (HEC), just to provide a few possibilities. In one particular aspect of this form, the thickener included in pesticide composition 12 is a fumed silica material that is aftertreated with dimethyldichlorosilane. One particular form of this type of thickener is available commercially from Evonik Industries (Esesen, Germany) as Aerosil® R 972. In one form in which pesticide composition 12 includes a thickener, the thickener is present in the range of 1%-6% by weight based on the total weight of capsule 10. In another form, the thickener is present in the range of 2%-5% by weight based on the total weight of capsule 10. In yet another form, the thickener is present in the range of 2%-4% by weight based on the total weight of capsule 10, although other values for the weight percentage of the thickener are contemplated.

Figure 2:
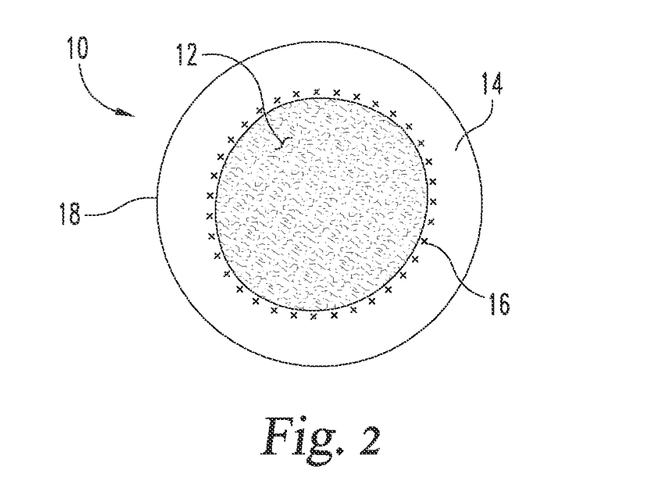
FIG. 2 is a section view of the capsule of FIG. 1 and schematically illustrates a cross-linked portion of the capsule shell wall.

In another form, pesticide composition 12 includes the pesticide, and a cross-linking agent in addition to or in lieu of the thickener. Non-limiting examples of cross-linking agents that may be included in pesticide composition 12 include dialdehydes such as ethanedial or glyoxal. In forms in which pesticide composition 12 includes a cross-linking agent, it may be present in the range of 0.05%-2.0% by weight based on the total weight of pesticide composition 12. In another form, the cross-linking agent is present in the range of 0.1%-1.5% by weight based on the total weight of pesticide composition 12. In yet another form, the cross-linking agent is present in the range of 0.2%-1.0% by weight based on the total weight of pesticide composition 12. In still another form, the cross-linking agent is present in the range of 0.2%-0.9% by weight based on the total weight of pesticide composition 12. In another form, the cross-linking agent is present in the range of 0.25%-0.8% by weight based on the total weight of pesticide composition 12. In still another form, the cross-linking agent is present in the range of 0.05%-0.11% by weight based on the total weight of pesticide composition 12. In another form, the cross-linking agent is present in the range of 0.06%-0.10% by weight based on the total weight of pesticide composition 12. In yet another form, the cross-linking agent is present in the range of 0.07%-0.09% by weight based on the total weight of pesticide composition 12, although other values for the weight percentage of the cross-linking agent are contemplated. In one or more of these or other forms, the amount of the cross-linking agent included in pesticide composition 12 is selected to provide a cross-linking effect to the gelatin material of shell wall 14 in an area that immediately surrounds pesticide composition 12 but does not extend throughout the entire thickness of shell wall 14. One non-limiting form of capsule 10 having this configuration is schematically illustrated in FIG. 2. In this form, the cross-linked portion 16 of shell wall 14 extends outwardly from pesticide composition 12 toward but terminates well short of external surface 18. It should be appreciated that the outward most extent of cross-linked portion 16 of shell wall 14 can be controlled by adjusting the amount of the cross-linking agent included in pesticide composition 12.

It is also contemplated that other pesticides could be included, either singularly or in combination, in pesticide composition 12 in addition to or in lieu of the fumigant. Non-limiting examples of such pesticides include insecticides such as antibiotic insecticides, macrocyclic lactone insecticides (for example, avermectin insecticides, milbemycin insecticides, and spinosyn insecticides), arsenical insecticides, botanical insecticides, carbamate insecticides (for example, benzofuranyl methylcarbamate insecticides, dimethylcarbamate insecticides, oxime carbamate insecticides, and phenyl methylcarbamate insecticides), diamide insecticides, desiccant insecticides, dinitrophenol insecticides, fluorine insecticides, formamidine insecticides, inorganic insecticides, insect growth regulators (for example, chitin synthesis inhibitors, juvenile hormone mimics, juvenile hormones, moulting hormone agonists, moulting hormones, moulting inhibitors, precocenes, and other unclassified insect growth regulators), nereistoxin analogue insecticides, nicotinoid insecticides (for example, nitroguanidine insecticides, nitromethylene insecticides, and pyridylmethylamine insecticides), organochlorine insecticides, organophosphorus insecticides, oxadiazine insecticides, oxadiazolone insecticides, phthalimide insecticides, pyrazole insecticides, pyrethroid insecticides, pyrimidinamine insecticides, pyrrole insecticides, tetramic acid insecticides, tetronic acid insecticides, thiazole insecticides, thiazolidine insecticides, thiourea insecticides, urea insecticides, as well as, other unclassified insecticides.

More particular examples of insecticides include, but are not limited to, 1 abamectin, acephate, acetamiprid, acethion, acetoprole, acrinathrin, acrylonitrile, alanycarb, aldicarb, aldoxycarb, aldrin, allethrin, allosamidin, allyxycarb, alpha-cypermethrin, alpha-endosulfan, amidithion, aminocarb, amiton, amitraz, anabasine, athidathion, azadirachtin, azamethiphos, azinphos-ethyl, azinphos-methyl, azothoate, barium hexafluorosilicate, barthrin, bendiocarb, benfuracarb, bensultap, beta-cyfluthrin, beta-cypermethrin, bifenthrin, bioallethrin, bioethanomethrin, biopermethrin, bioresmethrin, bistrifluron, borax, boric acid, boric acid, bromfenvinfos, bromocyclen, bromo-DDT, bromophos, bromophos-ethyl, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, chlorantraniliprole, chlorbicyclen, chlordane, chlordecone, chlordimeform, chlorethoxyfos, chlorfenapyr, chlorfenvinphos, chlorfluazuron, chlormephos, chloroform, chloropicrin, chlorphoxim, chlorprazophos, chlorpyrifos, chlorpyrifos-methyl, chlorthiophos, chromafenozide, cinerin I, cinerin II, cismethrin, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyclethrin, cycloprothrin, cyfluthrin, cyhalothrin, cypermethrin, cyphenothrin, cyromazine, cythioate, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphon, diafenthiuron, dialifos, diatomaceous earth, diazinon, dicapthon, dichlofenthion, dichlorvos, dicresyl, dicrotophos, dicyclanil, dieldrin, diflubenzuron, dilor, dimefluthrin, dimefox, dimetan, dimethoate, dimethrin, dimethylvinphos, dimetilan, dinex, dinoprop, dinosam, dinotefuran, diofenolan, dioxabenzofos, dioxacarb, dioxathion, disulfoton, dithicrofos, d-limonene, DNOC, doramectin, ecdysterone, emamectin, EMPC, empenthrin, endosulfan, endothion, endrin, EPN, epofenonane, eprinomectin, esfenvalerate, etaphos, ethiofencarb, ethion, ethiprole, ethoate-methyl, ethoprophos, ethyl formate, ethyl-DDD, ethylene dichloride, ethylene oxide, etofenprox, etrimfos, EXD, famphur, fenamiphos, fenazaflor, fenchlorphos, fenethacarb, fenfluthrin, fenitrothion, fenobucarb, fenoxacrim, fenoxycarb, fenpirithrin, fenpropathrin, fensulfothion, fenthion, fenthion-ethyl, fenvalerate, fipronil, flonicamid, flubendiamide, flucofuron, flucycloxuron, flucythrinate, flufenerim, flufenoxuron, flufenprox, fluvalinate, fonofos, formetanate, formothion, formparanate, fosmethilan, fospirate, fosthietan, furathiocarb, furethrin, gamma-cyhalothrin, gamma-HCH, halfenprox, halofenozide, HCH, HEOD, heptachlor, heptenophos, heterophos, hexaflumuron, HHDN, hydramethylnon, hydrogen cyanide, hyprone, hyquincarb, imidacloprid, imiprothrin, indoxacarb, iodomethane, IPSP, isazofos, isobenzan, isocarbophos, isodrin, isofenphos, isoprocarb, isoprothiolane, isothioate, isoxathion, ivermectin, jasmolin I, jasmolin II, jodfenphos, juvenile hormone I, juvenile hormone II, juvenile hormone III, kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, mephosfolan, mercurous chloride, mesulfenfos, metaflumizone, methacrifos, methamidophos, methidathion, methiocarb, methocrotophos, methomyl, methoprene, methoxychlor, methoxyfenozide, methylchloroform, methylene chloride, metofluthrin, metolcarb, metoxadiazone, mevinphos, mexacarbate, milbemectin, milbemycin oxime, mipafox, mirex, monocrotophos, morphothion, moxidectin, naftalofos, naled, naphthalene, nicotine, nifluridide, nitenpyram, nithiazine, nitrilacarb, novaluron, noviflumuron, ometheate, oxamyl, oxydemeton-methyl, oxydeprofos, oxydisulfoton, para-dichlorobenzene, parathion, parathion-methyl, penfluron, pentachlorophenol, permethrin, phenkapton, phenothrin, phenthoate, phorate, phosalone, phosfolan, phosmet, phosnichlor, phosphamidon, phosphine, phoxim, phoxim-methyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, profenofos, profluthrin, promacyl, promecarb, propaphos, propetamphos, propoxur, prothidathion, prothiofos, prothoate, protrifenbute, pyraclofos, pyrafluprole, pyrazophos, pyresmethrin, pyrethrin I, pyrethrin II, pyridaben, pyridalyl, pyridaphenthion, pyrifluquinazon, pyrimidifen, pyrimitate, pyriprole, pyriproxyfen, quassia, quinalphos, quinalphos-methyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sophamide, spinetoram, spinosad, spiromesifen, spirotetramat, sulcofuron, sulfluramid, sulfotep, sulfuryl fluoride, sulprofos, tau-fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetramethrin, theta-cypermethrin, thiacloprid, thiamethoxam, thicrofos, thiocarboxime, thiocyclam, thiodicarb, thiofanox, thiometon, thiosultap, thuringiensin, tolfenpyrad, tralomethrin, transfluthrin, transpermethrin, triarathene, triazamate, triazophos, trichlorfon, trichlormetaphos-3, trichloronat, trifenofos, triflumuron, trimethacarb, triprene, vamidothion, vaniliprole, XMC, xylylcarb, zeta-cypermethrin, zolaprofos, and α-ecdysone.

For more information consult "COMPENDIUM OF PESTICIDE COMMON NAMES" located at http://www.alanwood.net/pesticides/index.html. Also consult "THE PESTICIDE MANUAL" 14th Edition, edited by C D S Tomlin, copyright 2006 by British Crop Production Council.

As indicated above, various properties of capsule 10 can be altered to control characteristics of the release of pesticide composition 12 therefrom. In addition to or in lieu of modifying these properties, capsule 10 may also include a protease enzyme on its exterior surface to accelerate degradation of capsule 10 and the resulting release of pesticide composition 12 therefrom. Non-limiting examples of protease enzymes that could be included on capsule 10 include pepsin, trypsin, ficin, bromelain, papain, rennin and chymotrypsin. Variations in the acceleration of degradation of capsule 10 caused by the protease enzyme can be controlled by modifying the concentration of the enzyme. For example, it should be appreciated that higher enzyme concentrations will result in faster capsule degradation and release of pesticide composition 12 therefrom. Similarly, time profiles of the degradation of capsule 10 and the resultant release of pesticide composition 12 therefrom can be experimentally determined in order to facilitate the design of capsules 10 having release profiles tailored for particular applications. For example, in one particular instance where release of pesticide composition 12 from capsule 10 is desired to begin within a few hours of its application to a locus where pest control is desired, capsule 10 may be provided with a requisite amount and/or concentration of the enzyme to achieve such release. In other forms where a greater period of time is desired between the application of capsule 10 at the locus and the initiation of release of pesticide composition 12 therefrom, the amount and/or concentration of the enzyme can be modified as necessary.

In one form, the protease enzyme is dissolved in water to provide an enzyme solution that is applied to the external surface of capsule 10. Optional components that could be included in this solution include thickeners, stabilizers or extenders, just to provide a few non-limiting examples. The protease enzyme may also be applied to the external surface of capsule 10 in a dust or powder form. Non-limiting examples of dusts or powders in which the enzyme may be mixed include kaolin clay, ground volcanic rock, attapulgite clays, montmorillonite clays, diatomaceous earths, talc, bentonite, calcium carbonate and white carbon. In one particular but non-limiting form, a powder including a mixture of the enzyme and lactose is applied to capsule 10. One optional component that could be included in these dusts or powders is a surfactant, although the inclusion of additional components is also contemplated.

Capsule 10 may be formed utilizing any conventional encapsulation technique known in the art including, by way of non-limiting example, a rotary die encapsulation process. In this process, the materials forming shell wall 14 are provided as a heated, flowable mixture that is deposited on opposite cooling drums to form separate ribbons. These ribbons are conveyed to an injection wedge by a series of rollers, and the injection wedge guides the ribbons between a pair of oppositely positioned die rolls which couple the ribbons together to form a capsule. Before the ribbons are entirely coupled, the pesticide composition is injected therebetween by the injection wedge. After formation, the capsules may further undergo a drying step. Depending on the materials used in connection with capsule 10, regular maintenance of the rotary die apparatus may be necessary to avoid corrosion of various working surfaces, moving parts, or other components. For example, in one form in which 1,3-dichloropropene is included in pesticide composition 12, it may be necessary to ensure that various lubricating materials are regularly changed in order to avoid corrosion.

The locus to which capsule 10 may be applied can be any locus inhabited by a pest including, for example, vegetable crops, fruit and nut trees, grape vines, ornamental plants, domesticated animals, the interior or exterior surfaces of buildings, and the soil around buildings. Controlling pests generally means that pest populations, activity, or both, are reduced in a locus. This can come about when: pest populations are repulsed from a locus; when pests are incapacitated in or around a locus; or pests are exterminated, in whole or in part, in or around a locus. Of course a combination of these results can occur.

In one particular application, capsule 10 is placed on the surface of soil or buried in the soil. In either case, capsule 10 may be positioned utilizing a variety of different techniques. For example, when it is applied on the surface of soil, capsule 10 may be hand placed or dispersed with a broadcast or other type of mechanical spreader. Non-limiting burial techniques include the formation of trenches, holes, or other openings in the soil in which one or more capsules 10 are placed and then covered by soil. The particular spacing and depth at which capsule 10 is buried may depend on a variety of factors, including for example, soil type, targeted pests, and degree of infestation.

At some time after burial, shell wall 14 of capsule 10 will gradually degrade by, for example, breaking apart or fracturing as a result of swelling. When present, the enzyme on capsule 10 also causes its degradation. Upon gradual degradation of capsule 10, the resultant release of pesticide composition 12 from capsule 10 is also gradual. However, forms in which the degradation of capsule 10 and the release of pesticide composition 12 therefrom are more sudden are also possible. When pesticide composition 12 includes a fumigant in a liquid form for example, it will vaporize and penetrate the soil surrounding the original burial location of capsule 10 after being released therefrom. It should be understood that the length of time required for pesticide composition 12 to be released from capsule 10 following its burial will depend on a variety of factors, including for example, the physical properties of capsule 10 and/or the temperature, moisture, and pH of the soil. The length of time required for pesticide composition 12 to be released from capsule 10 following its burial will also depend, where applicable, on the amount and/or concentration of the enzyme provided on capsule 10. In certain forms, including those where capsule 10 includes an enzyme, it may be desirable to irrigate the soil where capsule 10 has been positioned in order to increase its moisture content for promoting degradation of capsule 10. For example, in some instances the soil can be irrigated until a moisture content in the range of 20%-40% of the soil is achieved.

EXAMPLES

The examples are for illustration purposes and are not to be construed as limiting the invention disclosed in this document to only the embodiments disclosed in these examples.

Example I

Capsule Production

A capsule fill mixture was prepared by adding 0.48 kg of Aerosil® R 972 (Evonik Industries, Essen, Germany) to 11.6 kg of 1,3-dichloropropene using moderate agitation. Agitation was continued taking care to avoid drawing air into the mixture until it was homogeneous (approximately 10 minutes).

A capsule shell material was prepared by first heating 8.7 kg of water and 2.6 Kg of Sorbitol Special™ (SPI Pharma, Wilmington, Del.) to 70° C. in a jacketed vessel and then adding 8.7 kg of 270 bloom type B gelatin (270 Bloom Lime Bone Gelatin, ZA-B270-2, Eastman Gelatine, Peabody, Mass.) to it with sufficient agitation to completely wet the gelatin. Care was taken to avoid drawing air into the mixture or otherwise creating foam. After the gelatin was wetted, the batch temperature was reduced to 60° C. and a vacuum drawn on the vessel to de-aerate the material. When de-aerated, the gelatin was a clear, dark caramel color.

The 1,3-dichloropropene-Aerosil® R 972 mixture was encapsulated using an R&D 4" Softgel Pilot Plant (CapPlus Technologies, Phoenix, Ariz.) fitted with #20 round dies to produce 1 ml capsules (12.7 mm diameter spherical) or #40 dies to produce 2 ml capsules (15.7 mm diameter spherical). The chill rolls on the encapsulator were set to 18-20° C. and the gap between the spreader box and chill roll was set to 0.9 mm. The spreader box temperature was set to 60° C. and the wedge temperature was set to 39-41° C. or the temperature required for the particular gelatin in use to create a successful seal. The encapsulation machine was operated at a speed of 4.5 rpm, equivalent to 20 liters/hour of 1,3-dichloropropene-Aerosil® R 972 mixture feed and approximately 6 liters per hour of gelatin-sorbitol-water mixture feed. The gel capsules produced were dried in a tumble dryer for 15 minutes and then transferred to trays for air drying for 24 to 48 hours. Encapsulation and drying were done at an ambient temperature of 18-21° C. and 30-35% relative humidity. The composition of the produced gel capsules is provided in Table 1:

TABLE 1

| Component | Component Wt % |
|---|---|
| 1,3-dichloropropene | 72.95 |
| gelatin | 15.07 |
| Sorbitol Special ™ | 4.68 |
| epoxidized soybean oil | 1.12 |
| Aerosil ® R 972 | 3.14 |
| impurities from tech. | 1.21 |
| water | 1.83 |

Example II

Determination of 1,3-Dichloropropene Loss from Capsules

Gel capsules from Example I above (capsules A) were compared to gel capsules having a wall made from 150-200 low-bloom gelatin (capsules B) with respect to 1,3-dichloropropene (1,3-D) lost therefrom. Each of capsules A and B had a 1 mL volume and was in the form of a 12.7 mm diameter sphere. Capsules A and B were placed in 10 mL size glass vials (one capsule/vial) and sealed with crimp tight caps. The vials were stored at room temperature or at 40° C. for the times indicated in Table 2.

The head space in each vial was then analyzed by using a gas tight syringe to take a 500 microliter sized sample and injecting the sample into a Model HP6890 gas chromatograph equipped with a 25 meter DB-5MS column (25 mm×0.52 um) and an FID detector. The amount of cis/trans-1,3-dichloropropene in each injected sample was measured as the peak area counts from the FID detector and was compared to relevant standard samples to determine the amount of 1,3-D in the headspace (amount lost from the capsule). The results are provided in Table 2.

TABLE 2

| Gel Capsule | Gel Capsule Core | Storage Conditions | Headspace Peak Area Counts (cis + trans) | 1,3-D Lost From Capsule Relative to Initial (% wt/wt) |
|---|---|---|---|---|
| A | 1,3-D/Aerosil ® R 972 | 5 days @ room temp | 0 | 0 |
| A | 1,3-D/Aerosil ® R 972 | 5 days @ 40° C. | 734 | 0.007 |
| A | 1,3-D/Aerosil ® R 972 | 10 days @ room temp | 0 | 0 |
| A | 1,3-D/Aerosil ® R 972 | 10 days @ 40° C. | 19732 | 0.2 |
| B | 1,3-D | 2 days @ room temp | 240516 | 2.45 |
| B | 1,3-D | 7 days @ room temp | 422816 | 4.32 |
| B | 1,3-D | 7 days @ 40° C. | 1624012 | 16.57 |

Example III

Capsule Field Trials

Field trials for the gel capsules of Example I were established under commercial conditions in banana production areas of Central America. Bananas were transplanted using commercial procedures typical of the area. Gel capsules according to Example I were used as a post-plant treatment. A commercial standard was also included as a comparison in each test. Treatments and use rates for both field trials are included in the Tables 3 and 4 below. Location 1 included four replications for each treatment and location 2 included three replications.

TABLE 3

| Location 1 | | | |
|---|---|---|---|
| Treatment number | Pesticide Treatment | Formulation | Pesticide Use rate |
| 1 | 1,3-dichloropropene | 1 mL gel caps | 5 L/Ha |
| 2 | 1,3-dichloropropene | 1 mL gel caps | 10 L/Ha |
| 3 | 1,3-dichloropropene | 1 mL gel caps | 15 L/Ha |
| 4 | 1,3-dichloropropene | 1 mL gel caps | 20 L/Ha |
| 5 | fenamiphos[1] | Granules | 5 Kg/Ha |

[1]Fenamiphos was supplied as Nemacur 15 G (Bayer)

TABLE 4

| Location 2 | | | |
|---|---|---|---|
| Treatment number | Pesticide Treatment | Formulation | Pesticide Use rate |
| 1 | 1,3-dichloropropene | 1 mL gel caps | 5 L/Ha |
| 2 | 1,3-dichloropropene | 1 mL gel caps | 10 L/Ha |
| 3 | 1,3-dichloropropene | 1 mL gel caps | 15 L/Ha |
| 4 | 1,3-dichloropropene | 1 mL gel caps | 20 L/Ha |
| 5 | cadusafos[1] | Granules | 3.5 Kg/Ha |

[1]Cadusafos was supplied as Rugby 10 G (FMC Corporation)

Gel caps were applied in the area immediately surrounding the base of the banana plant. Holes were made to a depth of 15-20 cm using a rod inserted into the soil. Gel caps were applied into the holes by hand and soil was reapplied into the holes to cover the gel caps. Commercial standards were formulated as granules and applied around the base of the plant without incorporation.

Several parameters were measured at intervals following application of the pesticide. Plant height and plant trunk diameter were evaluated over time at intervals of approximately two, four and six weeks after application of the pesticide. Root weight, percent functional roots and nematode counts were taken at intervals of 45 and 60 days after application (DAA). Plant height and trunk diameter were evaluated as direct measurements and are recorded in units of centimeters. Root weight, percent functional roots and nematode counts were obtained by separate soil samples which were taken and returned to the lab for analysis. Roots were separated from the soil and weighed. A separate, visual estimate was made to determine the percent of these roots that were healthy and functional. Nematode counts were made by extracting them from the roots and soil and then estimating the total by counting the actual number in sub-samples of the extracted materials.

Trends in most parameters measured were similar between the 1,3-D gel cap treatments and the commercial standard when measured over the evaluation periods (results shown in Tables 5 and 6). Most parameters showed an improvement over time. The overall conclusion is that 1,3-D applied via gel capsules according to Example I provides results comparable to commercial standards in both trial locations and was a viable alternative to existing commercial treatments.

TABLE 5

| Growth Parameter | Evaluation Time (DAA) | Treatment and Rate | | | | |
|---|---|---|---|---|---|---|
| | | 1,3-D @ 5 L/Ha | 1,3-D @ 10 L/Ha | 1,3-D @ 15 L/Ha | 1,3-D @ 20 L/Ha | fenamiphos @ 5 Kg/Ha |
| Plant Height (cm) | 14 | 164 | 176 | 173 | 174 | 162 |
| | 28 | 172 | 183 | 190 | 180 | 173 |
| | 42 | 182 | 191 | 201 | 190 | 182 |
| Root weight | 45 | 86 | 78 | 46 | 54 | 64 |
| | 60 | 48 | 68 | 34 | 47 | 46 |
| Stem diameter (cm) | 14 | 34 | 36 | 36 | 34 | 34 |
| | 28 | 38 | 40 | 41 | 38 | 37 |
| | 42 | 42 | 44 | 44 | 42 | 41 |
| Nematode count | 45 | 21,750a | 25,650a | 20,950a | 17,100a | 14,800a |
| | 60 | 38,400a | 30,400a | 40,150a | 40,400a | 26,500a |
| % Functional roots | 45 | 80 | 71 | 66 | 65 | 73 |
| | 60 | 83 | 83 | 72 | 67 | 83 |

TABLE 6

| Growth Parameter | Evaluation Time (DAA) | Treatment and Rate | | | | |
|---|---|---|---|---|---|---|
| | | 1,3-D @ 5 L/Ha | 1,3-D @ 10 L/Ha | 1,3-D @ 15 L/Ha | 1,3-D @ 20 L/Ha | cadusaphos @ 3.5 Kg/Ha |
| Plant Height (cm) | 15 | 143 | 150 | 147 | 145 | 143 |
| | 29 | 152 | 161 | 158 | 156 | 156 |
| | 43 | 161 | 168 | 169 | 165 | 169 |
| Root weight (gms) | 45 | 43 | 47 | 42 | 52 | 44 |
| | 60 | 74 | 61 | 37 | 75 | 53 |
| Stem diameter (cm) | 15 | 30 | 31 | 31 | 31 | 30 |
| | 29 | 33 | 34 | 35 | 34 | 33 |
| | 43 | 35 | 37 | 37 | 36 | 36 |
| Nematode count | 45 | 18,133a | 25,333a | 24,800a | 20,533a | 11,200a |
| | 60 | 17,200a | 22,400a | 18,933a | 25,200a | 23,733a |
| % Functional roots | 45 | 83 | 80 | 86 | 74 | 82 |
| | 60 | 81 | 84 | 81 | 91 | 86 |

Example IV

Cross-Linked Capsules—Preparation and Composition

Using the components and amounts shown in Table 7, gelatin capsules were prepared using various amounts of the gelatin cross-linking agent glyoxal. 1,3-dichloropropene (technical grade) was combined with Aerosil® R972 (Evonik Industries, Essen, Germany) under continuous agitation to form a smooth, homogeneous mixture with no entrained air. Glyoxal was combined with emulsifier Atlox™ 4851B (Croda Crop Care, Cowick Hall, East Yorkshire, England) and added to the 1,3-dichloropropene/Aerosil R972 mixture to form the pesticide composition as an emulsion. Pesticide composition samples were prepared with glyoxal concentrations of 0.0 (control) 0.25, 0.5 and 0.8% by weight.

The capsule shell material was prepared by first heating 7.24 kg of water and 3.16 Kg of Sorbitol Special™ (SPI Pharma, Wilmington, Del.) to 70° C. in a jacketed vessel and then adding 8.0 kg of 270 bloom type B gelatin (270 Bloom Lime Bone Gelatin, ZA-B270-2, Eastman Gelatine, Peabody, Mass.) to it with sufficient agitation to completely wet the gelatin. Care was taken to avoid drawing air into the mixture or otherwise creating foam. After the gelatin was wetted, the batch temperature was reduced to 60° C. and a vacuum drawn on the vessel to de-aerate the material. When de-aerated, the gelatin was a clear, dark caramel color.

The 1,3-dichloropropene/Aerosil® R972/glyoxal mixtures were each encapsulated with the gelatin prepared herein using the equipment and method described in Example I to produce 1 ml volume capsules. Each of the pesticide composition samples containing 0.0, 0.25, 0.5 and 0.8 weight % of glyoxal used to fill the gel capsules were fed sequentially with a sufficient transition time to allow the equipment to be cleared before starting a new concentration. The gel capsules produced were not tumble dried, but were immediately transferred to trays for air drying for 24 to 48 hours. Encapsulation and drying were done at an ambient temperature of 18-21° C. and 30-35% relative humidity.

TABLE 7

Gel Capsules Prepared with Glyoxal Cross-linker

| | Sample Number | | | |
|---|---|---|---|---|
| | 2A | 2C | 2D | 2E |
| Glyoxal in Pesticide Composition (before encapsulation, wt %) | 0.00 | 0.25 | 0.50 | 0.80 |

TABLE 7-continued

Gel Capsules Prepared with Glyoxal Cross-linker

| Component | Gel Capsule Composition (wt %) After Air Drying | | | |
|---|---|---|---|---|
| 1,3-Dichloropropene (tech. grade) | 72.27 | 72.09 | 71.91 | 71.69 |
| Atlox ™ 4851B | 3.01 | 3.00 | 3.00 | 2.99 |
| Glyoxal | 0.00 | 0.20 | 0.39 | 0.63 |
| Aerosil ® R972 | 3.14 | 3.13 | 3.12 | 3.11 |
| Gelatin | 15.07 | 15.07 | 15.07 | 15.07 |
| Sorbitol Special ™ | 4.68 | 4.68 | 4.68 | 4.68 |
| Water (residual) | 1.83 | 1.83 | 1.83 | 1.83 |
| Total | 100.00 | 100.00 | 100.00 | 100.00 |

Cross-Linked Capsules—Storage Stability

The gel capsules prepared with varying amounts of glyoxal cross-linker (0.00, 0.25, 0.50 and 0.80 wt %) in the pesticide composition (Table 7) were stored at 65° C. for 72 hours in 10 mL glass vials and were then analyzed for the loss of 1,3-dichloropropene from the gel capsule into the headspace of the vial as described in Example II. Three replications of each sample were analyzed and the Grubbs test (Grubbs, F. E., "Sample criteria for testing outlying observations," Annals of Mathematical Statistics, 21 (1950); Grubbs, F., "Procedures for detecting Outlying Observations in Samples," Technometrics, 11/1, 1-21 (1969)) was used to remove any statistical outliers from the data collected.

Figure 3:
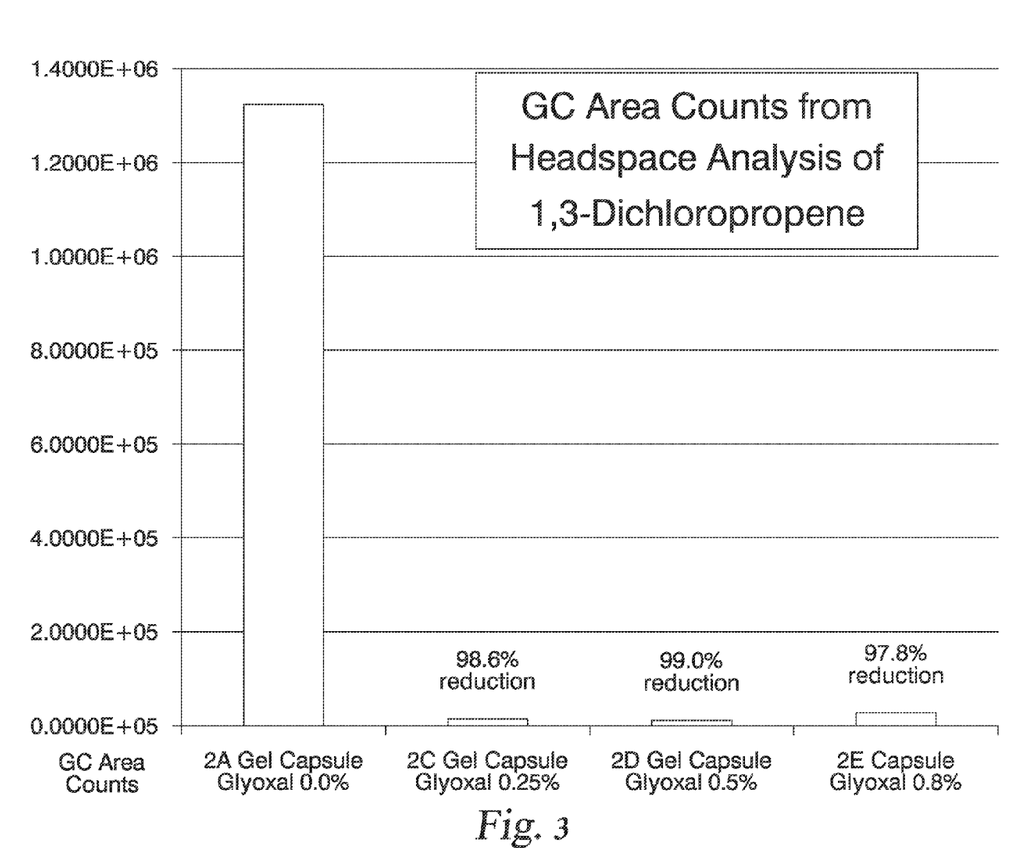
FIG. 3 is a graphical illustration of pesticide release from various capsules.

FIG. 3 shows the loss of 1,3-dichloropropene from the four types of gel capsules based on the GC area counts of a 500 microliter sample removed from the headspace of each storage vial. All three gel capsule samples prepared with glyoxal cross-linker showed a 97.8 to 99.0% reduction in the loss of 1,3-dichloropropene when compared to the control sample 2A.

Example V

Release of 1,3-Dichloropropene from Gel Capsules Placed in Soil

The following 1,3-dichloropropene samples shown in Table 8 were used in a soil release study described herein. Samples 2A and 2C were prepared as described in Example IV. Sample 2C-P was prepared by placing one gel capsule 2C in a 30 mL vial and adding 25 mg of papain enzyme to it. The papain enzyme was obtained from Biocatalysts, Batch #2485211. The capsule was gently agitated in the enzyme until evenly coated.

TABLE 8

| Sample | Composition | Source |
|---|---|---|
| Control | 1 mL liquid 1,3-dichloropropene | Supelco Lot LB73623, purity 99.9%; cis/trans 50.6/49.3 |
| 2A | 1 mL gel capsule | Example IV |
| 2C | 1 mL gel capsule cross-linked with 0.25% glyoxal | Example IV |
| 2C-P | 1 mL gel capsule cross-linked with 0.25% glyoxal and coated with papain enzyme | Example IV-V |

Soil and Soil Column Preparation

The soil was prepared by taking prescreened sandy loam soil and adding approximately 10 mL of water per 100 g of soil. The soil was placed in 6 inch tall by 4.25 inch wide cylindrical glass containers with one end sealed. Soil was placed in the glass containers to within approximately 1 inch from the top of the vessels. Finally, the 1,3-dichloropropene samples were applied to the soil in the containers by creating a hole in the center of the soil column and placing the sample at approximately half of the depth of the soil column. The samples were then covered with moistened soil.

Release of 1,3-Dichloropropene from Soil Columns

The release study was conducted by placing a soil column in an apparatus and flowing metered air at 1 liter/min across the top of the system and capturing the released 1,3-dichloropropene in activated carbon capture tubes. SKC air check samplers (SKC, Inc., Eighty Four, Pa., Model 224-PCXR8) were used to pull air through the carbon capture tubes. The air flow was metered across the carbon capture tubes in order to account for any loss of pressure resulting from restriction by the carbon capture tube. Anasorb® CSC (SKC, Inc., Eighty Four, Pa.) sample tubes containing coconut charcoal sorbent (catalog #226-16, 10×110 mm; 2 sections; 200+800 mg of sorbent; foam, glass wool & glass wool separators) were used to capture the volatilized 1,3-dicloropropene. The soil release study was conducted over a two week time period. Upon completion, the carbon capture tubes were extracted with 10 mL of hexane by use of a shaker for approximately 1 hour. An aliquot of the hexane extract was then analyzed by GC/MS.

Figure 4:
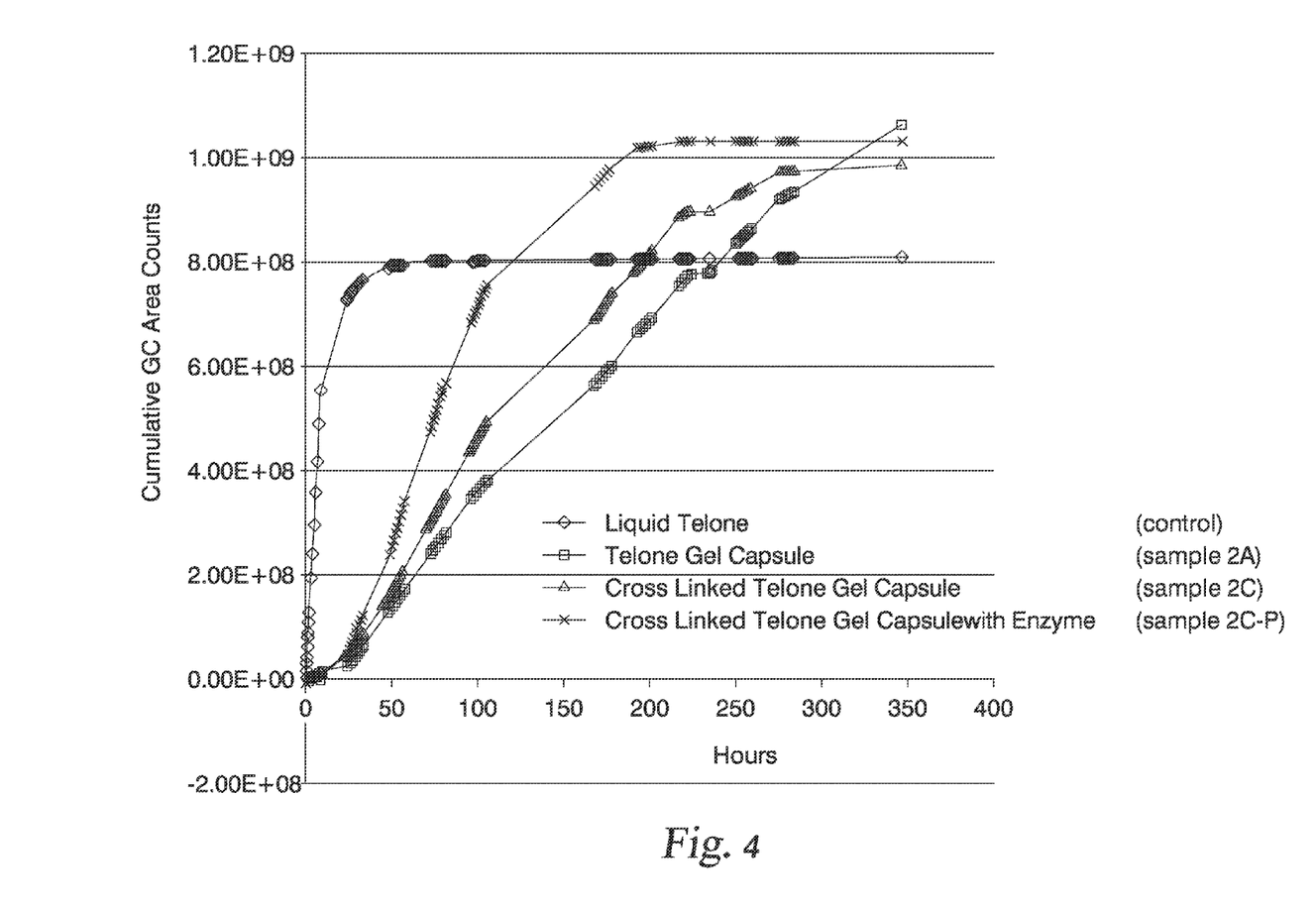
FIG. 4 is a graphical illustration of soil release profiles of a pesticide from various capsules.

The release profiles of the three 1,3-dichloropropene gel capsules and the liquid 1,3-dichloropropene control sample are shown in FIG. 4. All three of the gel capsules exhibited slower release of 1,3-dichloropropene compared to the liquid 1,3-dichloropropene control sample. Additionally, the papain enzyme coated gel capsule showed faster release of 1,3-dichloropropene compared to either of the other gel capsules.

In one embodiment, a capsule includes a shell wall encapsulating a pesticide composition and including a gelatin material having a Bloom strength in the range of 250 to 300 grams and a plasticizer composition. The gelatin material and the plasticizer composition are present at a ratio by weight between 2:1 and 4:1. In one form of this embodiment, the plasticizer composition includes a mixture of sorbitol and mannitol. In one aspect of this form, the mixture further includes sorbitol anhydrides. In another form of this embodiment, the gelatin material and the plasticizer composition are present at a weight ratio between 3:1 and 3.5:1. In still another form of this embodiment, the pesticide composition includes a fumigant. In one aspect of this form, the fumigant is 1,3-dichloropropene. In another aspect of this form, the pesticide composition further includes a fumed silica material. In a further aspect, the fumed silica material is hydrophobic and aftertreated with dimethyldichlorosilane. In yet another aspect of this form, the pesticide composition further includes a cross-linking agent. In a further aspect, the cross-linking agent is a dialdehyde. In an even further aspect, the dialdehyde is ethanedial. In still another aspect, the cross-linking agent is present in the range of 0.06% to 0.1% by weight based on total weight of the pesticide composition. In another form of this embodiment, the capsule the capsule further includes a protease enzyme. In one aspect of this form, the protease enzyme is a component of a powder mixture further including lactose. In another aspect of this form, the protease enzyme is selected from papain and bromelain.

In another embodiment, a capsule includes a shell wall including a gelatin material and a plasticizer composition that includes a mixture of sorbitol and mannitol. The capsule also includes a pesticide composition encapsulated by the shell wall, and the pesticide composition includes a fumigant and a fumed silica material. In one form of this embodiment, the gelatin material has a Bloom strength in the range of 250 to 300 grams. In another form of this embodiment, the gelatin material and the plasticizer composition are present at a ratio by weight between 2:1 and 4:1. In still another form of this embodiment, the mixture further comprises sorbitol anhydrides. In yet another form of this embodiment, the fumigant is 1,3-dichloropropene. In another form of this embodiment, the fumed silica material is hydrophobic and aftertreated with dimethyldichlorosilane. In still another form of this embodiment, the pesticide composition further includes a cross-linking agent. In one aspect of this form, the cross-linking agent is a dialdehyde. In a further aspect, the dialdehyde is ethanedial. In another form of this embodiment, the capsule further includes a protease enzyme. In one aspect of this form, the protease enzyme is a component of a powder mixture further including lactose. In another aspect of this form, the protease enzyme is selected from papain and bromelain.

In yet another embodiment, a capsule includes a shell wall formed by a gelatin composition and encapsulating a pesticide composition. The pesticide composition includes a fumigant, a fumed silica material and a dialdehyde cross-linking agent. In one form of this embodiment, the fumed silica material is hydrophobic and aftertreated with dimethyldichlorosilane. In another form of this embodiment, the dialdehyde cross-linking agent is ethanedial. In still another form of this embodiment, the cross-linking agent is present in the range of 0.06% to 0.1% by weight based on total weight of the pesticide composition. In yet another form of this embodiment, the capsule further includes a protease enzyme selected from papain and bromelain. In another form of this embodiment, the gelatin composition includes type-B gelatin and a plasticizer including a mixture of sorbitol, mannitol and sorbitol anhydrides. In yet another form, the fumigant is 1,3-dichloropropene.

In still another embodiment, a process includes providing a first mixture including a fumed silica material and 1,3-dichloropropene; providing a second mixture including type-B gelatin and a plasticizer including a mixture of sorbitol, mannitol and sorbitol anhydrides; and encapsulating the first mixture in the second mixture using a rotary die apparatus.

Other embodiments includes methods or techniques involving the placement of one or more capsules at a locus where pest control is desired.

The headings in this document are for convenience only and must not be used to interpret any portion thereof.

While the invention has been illustrated and described in detail in the drawings and foregoing description, the same is to be considered as illustrative and not restrictive in character, it being understood that only certain embodiments have been shown and described and that all changes and modifications that come within the spirit of the inventions are desired to be protected. It should be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

What is claimed is:

1. A capsule, comprising a shell wall encapsulating a pesticide composition and including a gelatin material having a Bloom strength in the range of 270 to 300 grams and a plasticizer composition, wherein the gelatin material and the plasticizer composition are present at a ratio by weight between 2:1 and 4:1 and the pesticide composition includes 1,3-dichloropropene.

2. The capsule of claim 1, wherein the gelatin material and the plasticizer composition are present at a weight ratio between 3:1 and 3.5:1.

3. The capsule of claim 1, wherein the pesticide composition further includes a cross-linking agent.

4. The capsule of claim 3, wherein the cross-linking agent is a dialdehyde.

5. The capsule of claim 4, wherein the dialdehyde is ethanedial.

6. The capsule of claim 3, wherein the cross-linking agent is present in the range of 0.06% to 0.1% by weight based on total weight of the pesticide composition.

7. The capsule of claim 1, further comprising a protease enzyme.

8. The capsule of claim 7, wherein the protease enzyme is a component of a powder mixture further including lactose.

9. The capsule of claim 7, wherein the protease enzyme is selected from papain and bromelain.

10. A capsule, comprising:
   a shell wall including a gelatin material having a Bloom strength in the range of 270 to 300 grams and a plasticizer composition comprising a mixture of sorbitol and mannitol; and
   a liquid mixture comprising 1,3-dichloropropene and a fumed silica material encapsulated by the wall.

11. The capsule of claim 10, wherein the mixture further comprises sorbitol anhydrides.

12. The capsule of claim 10, wherein the fumed silica material is hydrophobic and aftertreated with dimethyldichlorosilane.

13. The capsule of claim 10, wherein the liquid mixture further includes a cross-linking agent.

14. A capsule, comprising a shell wall formed by a gelatin composition including a gelatin having a Bloom strength in the range of 270 to 300 grams and at least one plasticizer, the shell wall encapsulating a liquid mixture including 1,3-dichloropropene, a fumed silica material and from 0.05%-2.0% by weight based on the total of the liquid mixture of a glyoxal cross-linking agent.

15. The capsule of claim 14, wherein the fumed silica material is hydrophobic and aftertreated with dimethyldichlorosilane.

16. The capsule of claim 14, wherein the at least one plasticizer includes a mixture of sorbitol, mannitol and sorbitol anhydrides and the liquid mixture further includes an emulsifier.

17. A process, comprising:
   providing a liquid mixture including a fumed silica material, a glyoxal cross-linking agent and 1,3-dichloropropene;
   providing a second mixture including type-B gelatin having a Bloom strength in the range of 270 to 300 grams and a plasticizer including a mixture of sorbitol, mannitol and sorbitol anhydrides; and
   encapsulating the liquid mixture in the second mixture using a rotary die apparatus.

* * * * *